(12) United States Patent
Peng et al.

(10) Patent No.: US 10,391,531 B2
(45) Date of Patent: Aug. 27, 2019

(54) QUICK BLADE REPAIR AND REPLACEMENT ENABLED APPARATUS INTEGRATING MEDICAL WASTE CRUSHING AND STEAM TREATMENT

(71) Applicant: CHONGQING GIENT HEATING INDUSTRY CO., LTD, Chongqing (CN)

(72) Inventors: Jun Peng, Chongqing (CN); Zhe Wang, Chongqing (CN); Fengyan Chen, Chongqing (CN)

(73) Assignee: CHONGQING GIENT HEATING INDUSTRY CO., LTD, Chongqing (CN)

(*) Notice: Subject to any disclaimer, the term of this patent is extended or adjusted under 35 U.S.C. 154(b) by 269 days.

(21) Appl. No.: 15/665,430

(22) Filed: Aug. 1, 2017

(65) Prior Publication Data

US 2017/0326602 A1 Nov. 16, 2017

Related U.S. Application Data

(63) Continuation of application No. PCT/CN2016/088382, filed on Jul. 4, 2016.

(30) Foreign Application Priority Data

Jul. 6, 2015 (CN) .......................... 2015 1 0389509

(51) Int. Cl.
*A61L 2/00* (2006.01)
*A61L 9/00* (2006.01)
(Continued)

(52) U.S. Cl.
CPC .............. *B09B 3/0075* (2013.01); *A61L 2/07* (2013.01); *A61L 11/00* (2013.01); *B02C 18/10* (2013.01);
(Continued)

(58) Field of Classification Search
CPC . A61L 2/07; A61L 11/00; B02C 18/10; B02C 18/142; B02C 19/0075; B09B 3/0075
(Continued)

(56) References Cited

U.S. PATENT DOCUMENTS 5,620,654 A * 4/1997 Mosenson ............... A61L 11/00
422/28
5,656,248 A * 8/1997 Kline ....................... A61L 11/00
422/105
(Continued)

FOREIGN PATENT DOCUMENTS

CN 2342889 10/1999
CN 2587510 11/2003
(Continued)

OTHER PUBLICATIONS

"Office Action of Russia Counterpart Application" with English translation thereof, dated Aug. 6, 2018, p. 1-p. 25.

*Primary Examiner* — Monzer R Chorbaji
(74) *Attorney, Agent, or Firm* — JCIPRNET (57) ABSTRACT

A quick blade repair and replacement enabled apparatus integrating medical waste shredding and sterilization is a dismountable integrally assembled vertical structure. Three chambers, including a loading and stirring, a shredding and a sterilization and discharging chamber are connected into a whole. Two repair gates are respectively on the left and right sides of the shredding chamber, they are designed as a whole together with the rotary blade shaft, when repair and replace the blades, only the repair gates need to be dismounted, and the replacement process can be finished outside the shredding chamber. The stationary blades are pressed on the inner wall of the shredding chamber by using binder plate, and bolts for securing the binder plate are screwed from outside.

15 Claims, 6 Drawing Sheets

(51) Int. Cl.
    *B02C 13/00*     (2006.01)
    *B09B 3/00*     (2006.01)
    *A61L 2/07*     (2006.01)
    *A61L 11/00*     (2006.01)
    *B02C 18/10*     (2006.01)
    *B02C 18/18*     (2006.01)
    *B02C 19/00*     (2006.01)
    *B02C 18/14*     (2006.01)
    *B02C 18/22*     (2006.01)
    *B02C 18/16*     (2006.01)

(52) U.S. Cl.
    CPC ............ *B02C 18/142* (2013.01); *B02C 18/18* (2013.01); *B02C 18/2216* (2013.01); *B02C 19/0075* (2013.01); *B09B 3/0091* (2013.01); *B02C 2018/162* (2013.01); *B02C 2018/188* (2013.01)

(58) Field of Classification Search
    USPC ............... 422/26, 28, 32–33, 292, 295, 297, 422/299–300, 305, 307; 241/185.5
    See application file for complete search history.

(56) References Cited

U.S. PATENT DOCUMENTS 6,186,428 B1 * 2/2001 Robinson ............ B02C 19/0075
                                              241/100
2013/0284628 A1   10/2013  Moncrief et al.
2013/0287628 A1 * 10/2013  Smith, III ............ A61L 11/00
                                              422/26

FOREIGN PATENT DOCUMENTS

| | | |
|---|---|---|
| CN | 202238233 | 5/2012 |
| CN | 102940902 | 2/2013 |
| CN | 104148376 | 11/2014 |
| CN | 203991647 | 12/2014 |
| CN | 104525332 | 4/2015 |
| CN | 104587514 | 5/2015 |
| CN | 104984980 | 10/2015 |
| CN | 204734765 | 11/2015 |
| EA | 010188 | 6/2008 |
| JP | 2003001130 | 1/2003 |
| RU | 100403 | 12/2010 |

* cited by examiner

QUICK BLADE REPAIR AND REPLACEMENT ENABLED APPARATUS INTEGRATING MEDICAL WASTE CRUSHING AND STEAM TREATMENT

CROSS-REFERENCE TO RELATED APPLICATION

This is a continuation of International Application No. PCT/CN2016/088382, filed on Jul. 4, 2016, which claims the priority benefits of China Application No. 201510389509.4, filed on Jul. 6, 2015. The entirety of each of the above-mentioned patent applications is hereby incorporated by reference herein and made a part of this specification.

BACKGROUND OF THE INVENTION

1. Field of the Invention

The present invention generally relates to a medical waste treatment apparatus, in particular, to an integrated medical waste treatment apparatus integrating high temperature sterilization and crushing into a same confined space.

2. Description of Related Art

There exist various medical waste high-temperature steam treatment apparatuses. An integrated high-temperature steam treatment apparatus in which a shredder is designed in a medical waste high temperature sterilization container becomes a preferred apparatus for small and medium medical waste projects in worldwide hospitals because the apparatus highly integrates all treatment processes and completes the treatment processes all at once in a confined container. However, in such an integrated apparatus currently known, convenience and quickness in replacement and repair of internal components of the machine are not achieved due to a structure design of the apparatus. When the shredder is repaired or blades are replaced, dismounting is quite difficult, an operation environment is poor, and a crane or special-purpose lifting equipment is needed to lift an entire blade shaft of the shredder out of the sterilization container before the blades can be replaced or the shredder can be repaired. An apparatus in which a feeding chamber, a shredding chamber, and a discharging chamber are integrated in sections is also designed, but the design for the shredding chamber still cannot resolve the problems of difficulty in repair of the shredder and blade replacement that consumes much time and energy. When the blades are dismounted/mounted and repaired, other chambers or apparatuses connected to the shredding chamber need to be dismounted, and this needs additional special-purpose lifting equipment.

In a process of treating medical waste by using high-temperature steam, crushing is an indispensable link. The medical waste often contains not only hard materials, but also flexible soft materials, and even metal devices such as a surgical clamp may be mixed in the medical waste. Due to such a special and complex characteristic, blades of a shredder rapidly wear, have a relatively short service life, and need to be frequently dismounted/mounted and replaced.

Therefore, in actual use, blades of a medical waste shredder are most frequently repaired and replaced parts. Generally, damaged blades need to be replaced or repaired every month, and each time the blades are dismounted for repair and replacement, three to four people often need to work for three to four days, and lifting equipment is also needed. Not only a reducer, a bearing support, and other parts need to be dismounted, but also a chamber body in the apparatus needs to be dismounted by lifting or an entire blade roll of the shredder needs to be lifted out of a sterilization pressure container. Therefore, requirements on skills of the operators are high, labor intensity is high, and replacement time is long, greatly affecting the normal progress of medical waste treatment. The Medical Waste Management Regulations explicitly stipulates that "medical and health institutions should be equipped with temporary storage facilities and equipment for medical waste, and medical waste should not be stored in the open air; medical waste should not be temporarily stored for more than two days." The stipulation emphasizes the importance of continuous operation of medical waste treatment apparatuses from another perspective. Therefore, quick repair and maintenance is an extremely important technical indicator for medical waste treatment apparatuses.

SUMMARY OF THE INVENTION

Accordingly, the present invention is directed to a quick blade repair and replacement enabled apparatus integrating medical waste crushing and steam treatment, to resolve the problems in the prior art.

To achieve the foregoing objective, a quick blade repair and replacement enabled apparatus integrating medical waste crushing and steam treatment provided in the present invention is an integrally assembled vertical structure capable of being disassembled. The apparatus sequentially includes three chamber bodies, connected into a whole by using flanges and bolts, of a feeding and stirring chamber, a shredding chamber, and a sterilization and discharging chamber from top to bottom. The three chamber bodies internally form a communicating sealable space, and are vertically placed on a support frame as a whole. A power mechanism is provided outside a chamber body of the shredding chamber.

The structure of the shredding chamber is mainly improved in the present invention. A top end and a bottom end of the shredding chamber are respectively opening flange structures. A left side and a right side of chamber body of the shredding chamber are respectively provided with repair gates. A rotary blade assembly and a stationary blade assembly are provided in the shredding chamber. Two ends of a rotary blade shaft of the rotary blade assembly are respectively fixed on the repair gates by using bearings. Bearing supports form a whole structure with the repair gates. One end of the rotary blade shaft extends out of the chamber body of the shredding chamber, and is connected to the power mechanism. The power mechanism uses a sprocket or a gear transmission structure. Rotary blades of the rotary blade assembly are mounted on the rotary blade shaft. Blade claws of adjacent rotary blades are arranged by staggering at an angle, and the rotary blades on the different rotary blade shafts are alternately arranged. Stationary blades of the stationary blade assembly are fixed on an inner wall of the chamber body of the shredding chamber by using pressing plates, and the pressing plates are secured from outside of the chamber body of the shredding chamber by using bolts. The rotary blades and the stationary blades are alternately arranged.

In the present invention, the left side and the right side of the shredding chamber are respectively provided with repair gates, such that and the repair gates of the shredder and the bearing supports for the rotary blade shaft are designed as a whole, when the blades of the shredder are repaired or replaced, only the repair gates need to be dismounted, and a replacement process can be completed outside the shredding chamber. In addition, the stationary blades are pressed on the inner wall of the chamber body of the shredding chamber by using the pressing plates, and the bolts for securing the pressing plates are screwed from outside to inside. When the blades are replaced, an operator also only needs to loosen the securing bolts outside the chamber body of the shredding chamber, and the blades can be replaced without the need to enter the machine.

Further, to achieve quicker and more convenient dismounting and mounting of the blade assemblies and ensure reliable working of the blade assemblies, in the apparatus, the repair gates of the shredder are designed as quick dismounting and mounting structures. Gate plates of the repair gates are connected and fixed to the chamber body of the shredding chamber by using bolts. The gate plates are provided with the bearing supports for mounting the bearings of the rotary blade shaft and cover plates for securing and sealing the bearings. The cover plate at one end of the rotary blade shaft is an open cover, and the rotary blade shaft passes through the open cover and is connected to the power mechanism outside the chamber body of the shredding chamber. The cover plate at the other end is a closed cover, for sealing the end of the rotary blade shaft.

Further, a relatively appropriate and reliable blade assembly design is a double-shaft and double-roller structure formed by two rotary blade assemblies and two stationary blade assemblies. The two rotary blade assemblies include the rotary blade shafts and the rotary blades and rotary blade separation rings mounted on the rotary blade shafts, and the rotary blades and the rotary blade separation rings are alternately mounted. The two stationary blade assemblies include the stationary blades and stationary blade separation rings, and the stationary blades and the separation rings are alternately mounted. The rotary blades are designed to be disk-shaped, and plural blade claws are provided on a circumference of the rotary blades. The stationary blades are designed to be sector-shaped. The two stationary blade assemblies are respectively alternately combined with the rotary blades and the rotary blade separation rings of the two rotary blade assemblies.

In the apparatus, the structure of the sterilization and discharging chamber is further improved. A top end of the sterilization and discharging chamber is designed as an opening flange, and a bottom of the sterilization and discharging chamber is provided with a quick-opening discharging gate. A discharging gate opening and closing mechanism and a secure interlocking mechanism ensuring secure opening and closing of the discharging gate are provided outside the chamber body of the sterilization and discharging chamber. Specially, a tray filtering gating mechanism is provided inside the chamber body of the sterilization and discharging chamber, so as to, first, quickly discharge materials in the chamber, second, prevent medical waste from being soaked in a condensate, and third, facilitate even steam penetration and heat conduction in a sterilization treatment process.

Specifically, the tray filtering gating mechanism includes a filtering cartridge, two four-link mechanisms, four connecting shafts, and two supporting plates. The filtering cartridge is connected to the inner wall of the chamber body of the sterilization and discharging chamber with a gap there between. Upper ends of the two four-link mechanisms are connected to an external link mechanism outside the chamber body of the sterilization and discharging chamber. The external link mechanism is driven by using an air cylinder or an oil cylinder. Lower ends of the two four-link mechanisms are connected to middle edges of the two supporting plates by using the four connecting shafts. The supporting plates are capable of turning at the connecting shafts. The two supporting plates may be arranged in bilateral symmetry and placed at a lower end of the filtering cartridge. External ends of the supporting plates are connected to the inner wall of the chamber body of the sterilization and discharging chamber by using hinges and are capable of turning at the hinges. When air or oil in the air cylinder or the oil cylinder expands or is compressed, the supporting plates open or close driven by the external link mechanism and the four-link mechanisms.

By means of the improved structure designs above, the apparatus overcomes the actual shortcoming of the need to lift an entire blade roller mechanism of a shredder by using lifting equipment, or the need to dismount a chamber body, or the need for an operator to enter the chamber body when blades of the shredder are replaced, improves working efficiency, and avoids that an operator enters a hazardous area. By using the apparatus, each time blades are replaced, usually the work can be successfully completed by only two people to spend a half day, greatly improving working efficiency. In addition, by means of the improved design for a sterilization and discharging chamber, materials in the chamber can be quickly discharged, and medical waste is prevented from being soaked in a condensate, and even steam penetration and heat conduction are facilitated in a sterilization treatment process, thereby achieving a better high temperature sterilization treatment effect.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The structure and the use manner of the apparatus are further described below with reference to the accompanying drawings.

Figure 1:
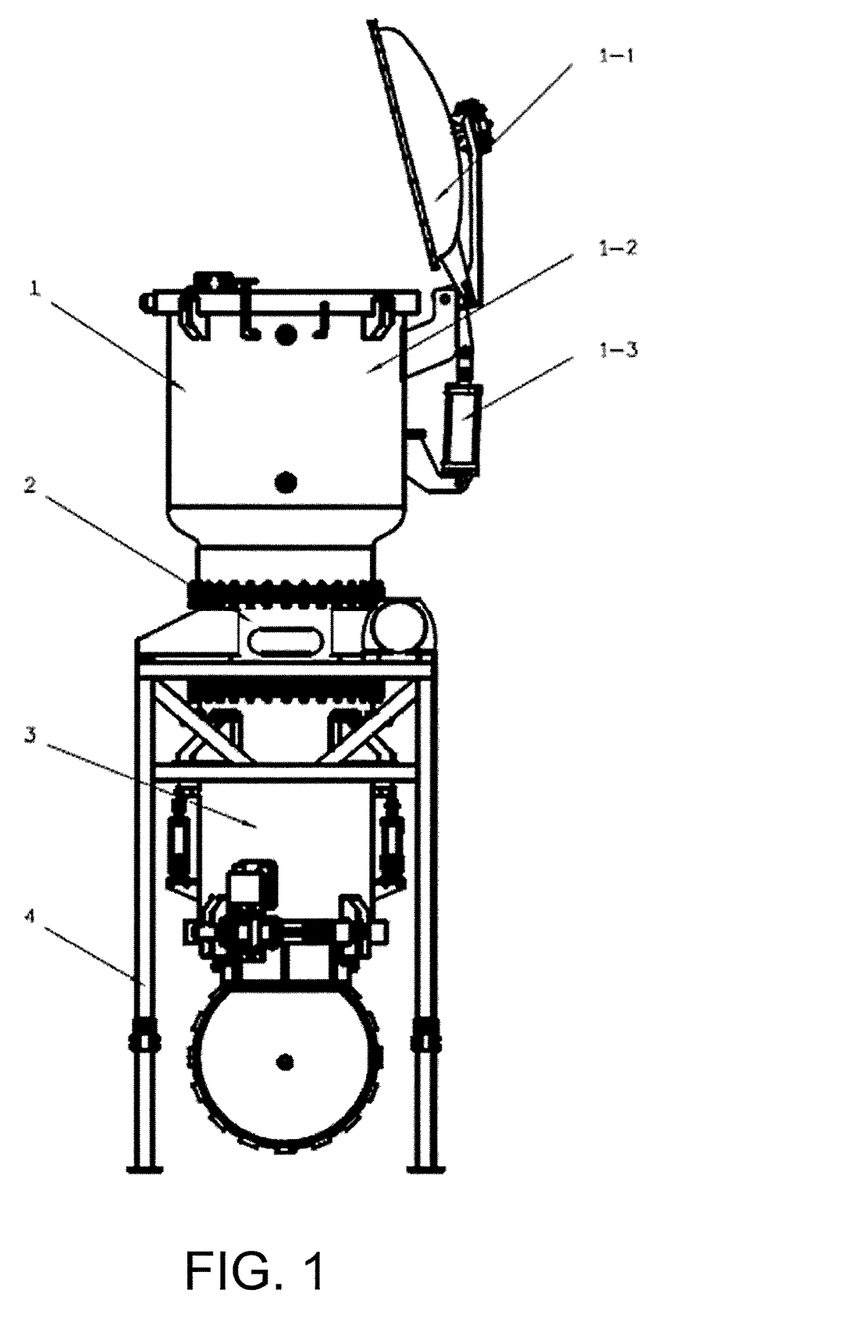
FIG. 1 is an overall schematic structural diagram of the apparatus.
Figure 1A:
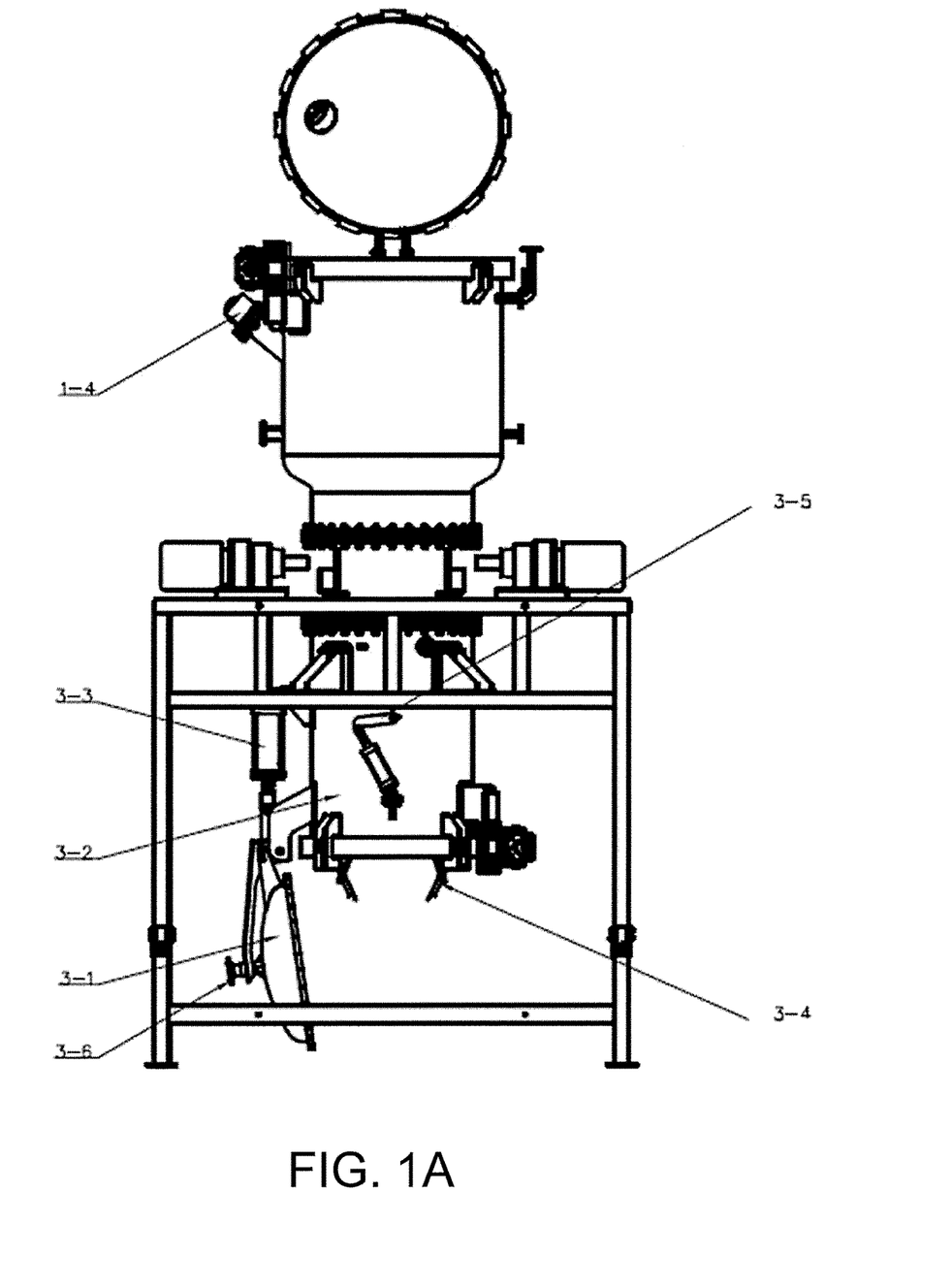
FIG. 1A is a left-side view of FIG. 1.

Referring to FIG. 1 and FIG. 1A, the apparatus is an integrally assembled vertical structure capable of being disassembled. The upper portion of the apparatus is a feeding and stiffing chamber 1, and the top of the feeding and stirring chamber 1 is a feeding gate 1-1 and a feeding gate opening and closing mechanism. The middle portion is a shredding chamber 2, and a crushing cutter mechanism is provided in the shredding chamber 2. The feeding and stirring chamber 1 is further provided with a pressing and stirring mechanism 1-4, and the pressing and stirring mechanism 1-4 passes through the feeding and stirring chamber 1. The lower portion of the feeding and stirring chamber 1 is connected to the shredding chamber 2, and the lower portion of the shredding chamber 2 is a sterilization and discharging chamber 3.

Three chamber bodies of the feeding and stirring chamber 1, the shredding chamber 2, and the sterilization and discharging chamber 3 of the apparatus are connected into a whole by using bolts. The three chamber bodies internally form a communicating sealable space, and are vertically placed on a support frame 4 as a whole. The lower end of the feeding and stirring chamber 1 is connected to the top end of the shredding chamber 2, and the lower end of the shredding chamber 2 is connected to the top end of the sterilization and discharging chamber 3.

A stirring apparatus 1-4 in the chamber body 1-2 of the feeding and stirring chamber 1 is obliquely inserted on the chamber body 1-2, a power part is outside the chamber body 1-2 of the feeding and stirring chamber 1, and a stirring part is inside the chamber body 1-2 of the feeding and stirring chamber 1.

Figure 2:
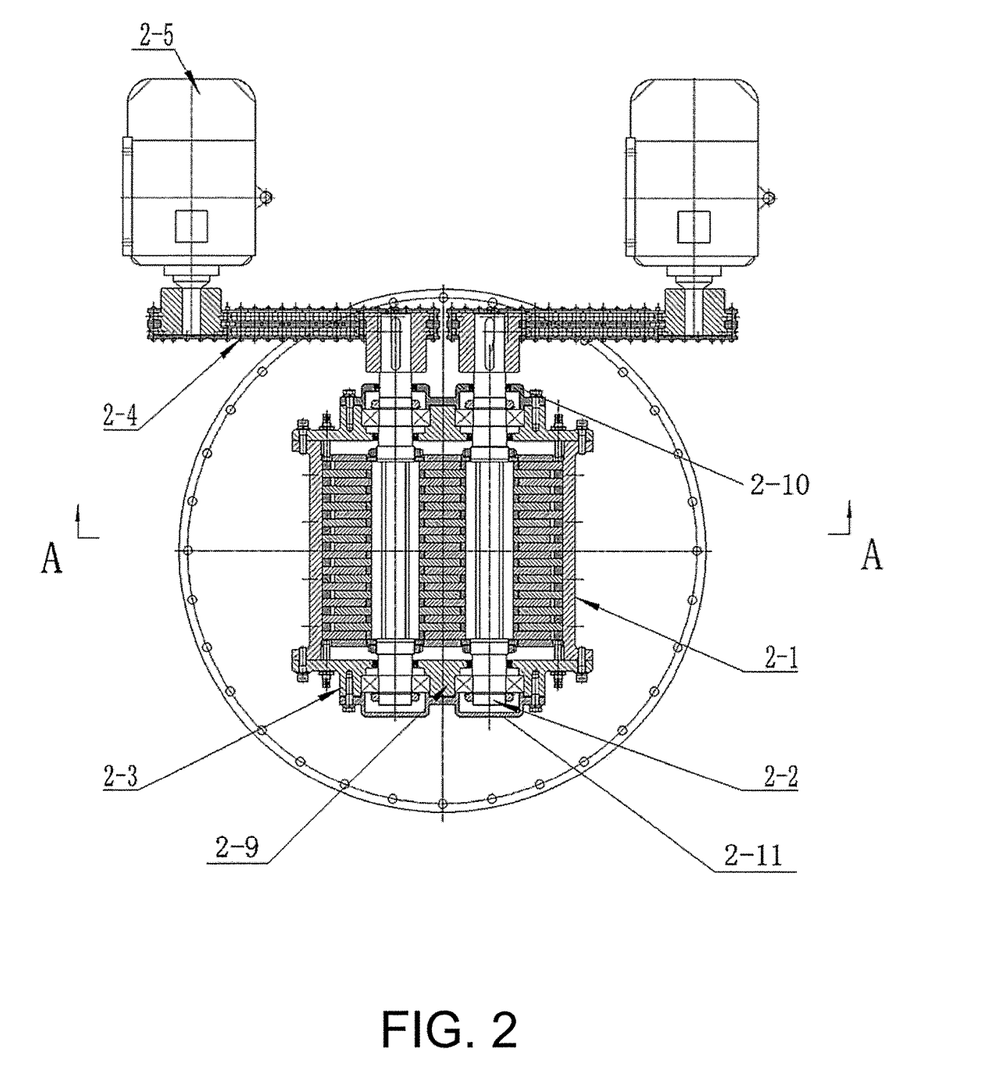
FIG. 2 is a schematic structural diagram of a shredding chamber.
Figure 2A:
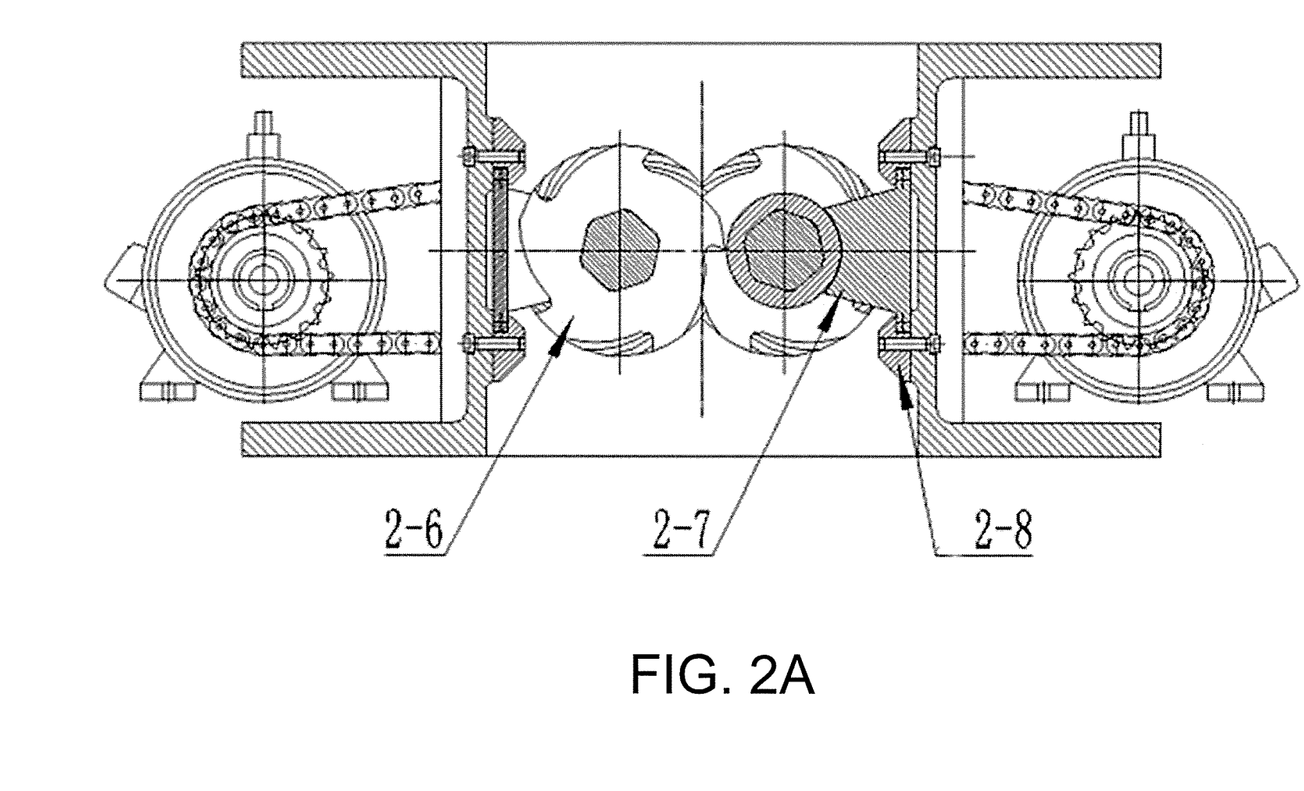
FIG. 2A is an A-A sectional view of FIG. 2.

Referring to FIG. 2 and FIG. 2A, the top end and the bottom end of the shredding chamber 2 are respectively opening flange structures, for connecting to the chamber bodies of the feeding and stirring chamber 1 and the sterilization and discharging chamber 3. The left side and the right side of the shredding chamber 2 are respectively provided with Repair gates 2-3. A double-shaft and double-roller structure formed by two rotary blade assemblies and two stationary blade assemblies is provided in the chamber body 2-1 of the shredding chamber 2.

The rotary blade assemblies include two rotary blade shafts 2-2 and rotary blades 2-6 and rotary blade separation rings mounted on the rotary blade shafts 2-2, and the rotary blades 2-6 and the rotary blade separation rings are alternately mounted along axial direction of the rotary blade shaft 2-2. Two ends of the rotary blade shafts 2-2 are fixed on the repair gates 2-3 of the chamber body 2-1 of the shredding chamber 2 by using bearings. Bearing supports 2-9 and the repair gates 2-3 are designed as a whole, and the bearing supports 2-9 may be dismounted with the repair gates 2-3 together. The bearing support 2-9 at one end of the rotary blade shafts 2-2 forms a whole structure with the repair gate 2-3, and one end of the rotary blade shafts 2-2 extends out and is connected to reducers 2-5 by using chain transmission (or gear transmission) mechanisms 2-4. Rotary blades 2-6 are provided on the rotary blade shafts 2-2. The rotary blades 2-6 are designed to be disk-shaped, and plural blade claws are provided on the circumference of the rotary blades 2-6. Blade claws of rotary blades 2-6 on the different rotary blade shafts 2-2 are alternately arranged by staggering at an angle.

The stationary blade assemblies include stationary blades 2-7 and stationary blade separation rings. The stationary blades 2-7 and the stationary blade separation rings are alternately mounted parallel to axial direction of the rotary blade shaft 2-2, and are fixed on the inner wall of the chamber body 2-1 of the shredding chamber 2 by using pressing plates 2-8, and the pressing plates 2-8 are secured from outside of the chamber body 2-1 of the shredding chamber 2 by using bolts. The stationary blades 2-7 are designed to be sector-shaped.

The two stationary blade assemblies are respectively alternately combined with the rotary blades 2-6 and the rotary blade separation rings of the two rotary blade assemblies.

For convenience in dismounting, the repair gates 2-3 have a quick dismounting and mounting structure. Gate plates of the repair gates 2-3 are connected and fixed to the chamber body 2-1 of the shredding chamber 2 by using bolts, and can be dismounted as a whole. Holes allowing the blade shafts to pass through are provided on the gate plates, and the bearing supports 2-9 structures are formed outside the holes, for mounting bearings and seal rings. Cover plates for securing and sealing the bearings are provided outside the gate plates and fixed by using bolts. The cover plate at one end of the rotary blade shafts 2-2 is an open cover 2-10, and the rotary blade shafts pass through the open cover 2-10 and are connected to power mechanisms 2-5 outside the chamber body 2-1 of the shredding chamber 2, and the cover plate at the other end is a closed cover 2-11, for sealing the ends of the rotary blade shafts 2-2.

During dismounting and mounting, only the repair gates 2-3 need to be dismounted and mounted. That is, first the closed cover 2-11 and the open cover 2-10 on the gates are dismounted, then the bearings and the seal rings are dismounted, then the bolts in the gate plates are dismounted, and finally the repair gate 2-3 on one side may be opened, which is convenient for a worker to fetch out the rotary blade assemblies.

When the stationary blade assemblies are dismounted and mounted, it is only needed to loosen, from outside of the chamber, the bolts for securing the pressing plates 2-8, and then the stationary blades 2-7 and the rotary blades 2-6 can be conveniently dismounted alternately one after one. That is, dismounting and mounting can be completed outside the chamber body 2-1 of the shredding chamber 2.

In addition, because the blade shafts of the shredding chamber 2 and the reducers are connected by using chain transmission or gear transmission, during repair and maintenance, only sprockets or belt pulleys on the blade shafts need to be dismounted, and the reducers do not need to be moved, thereby improving repair and maintenance efficiency.

Figure 3:
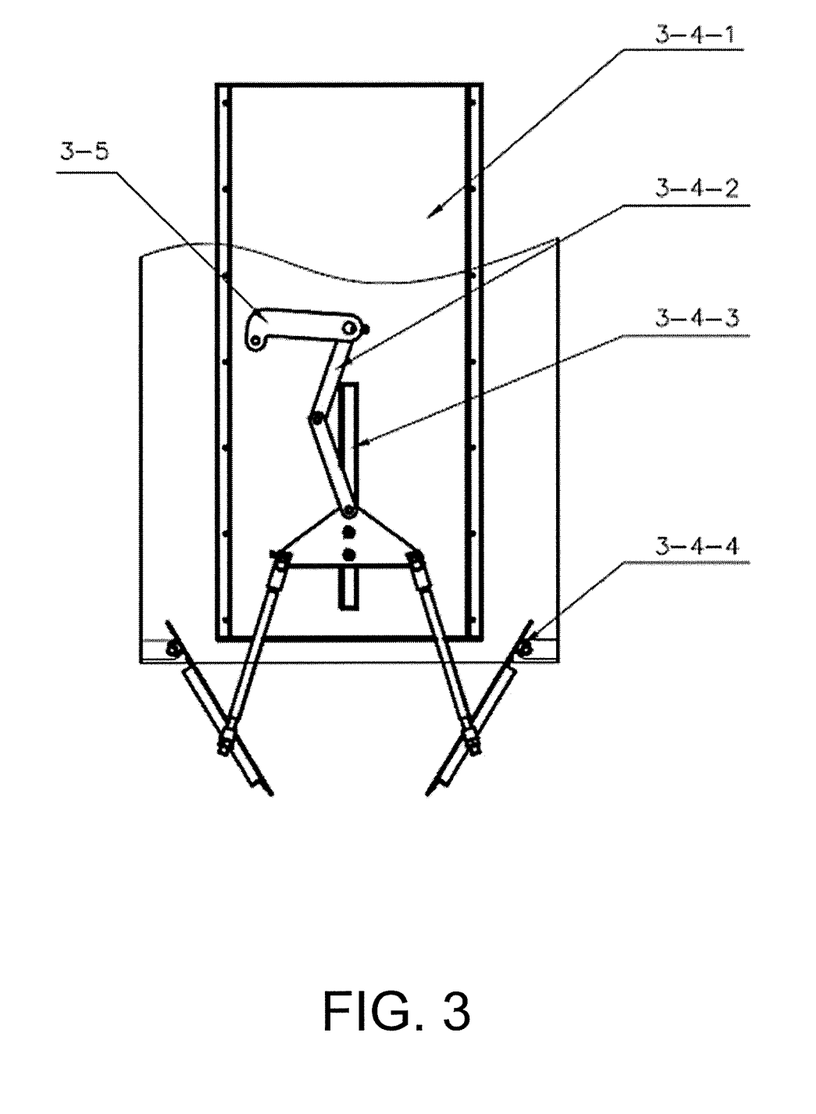
FIG. 3 is a schematic structural diagram of a sterilization and discharging chamber.
Figure 3A:
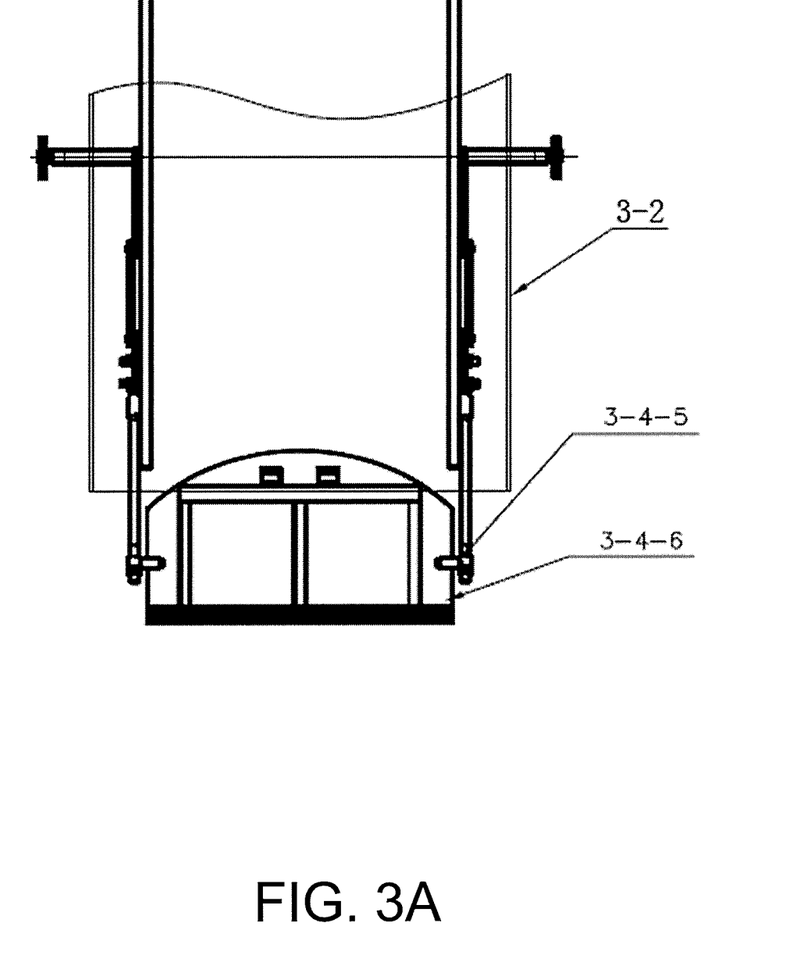
FIG. 3A is a left-side view of FIG. 3.

Referring to FIG. 3 and FIG. 3A, the top end of the sterilization and discharging chamber 3 is an opening flange structure, and the bottom of the sterilization and discharging chamber 3 is provided with a discharging gate 3-1. A discharging gate opening and closing mechanism 3-3 (including a secure interlocking mechanism 1-3 to ensure secure opening and closing of the discharging gate 3-1) is provided outside the chamber body 3-2 of the sterilization and discharging chamber 3. A tray filtering gating mechanism 3-4 is provided inside the chamber body 3-2 of the sterilization and discharging chamber 3.

The tray filtering gating mechanism 3-4 includes a filtering cartridge 3-4-1, two four-link mechanisms 3-4-2, two guide mechanisms 3-4-3, two hinges 3-4-4, four connecting shafts 3-4-5, and two supporting plates 3-4-6. The filtering cartridge 3-4-1 is connected to the inner wall of the chamber body 3-2 of the sterilization and discharging chamber 3 with a gap there between. One end of the two four-link mechanisms 3-4-2 is connected to an external link mechanism 3-5 provided outside the chamber body 3-2 of the sterilization and discharging chamber 3. The external link mechanism 3-5 is driven by using an air cylinder (or an oil cylinder). The other end of the two four-link mechanisms 3-4-2 is connected to middle edges of the two supporting plates 3-4-6 by using the four connecting shafts 3-4-5. The two supporting plates 3-4-6 are arranged in bilateral symmetry and placed below the filtering cartridge 3-4-1. The supporting plates 3-4-6 are capable of turning at the connecting shafts 3-4-5. The external ends of the supporting plates 3-4-6 are connected to the inner wall of the chamber body 3-2 of the sterilization and discharging chamber 3 by using the hinges 3-4-4, and the supporting plates 3-4-6 are capable of turning at the hinges 3-4-4. When air (or oil) in the air cylinder (or the oil cylinder) expands or is compressed, the supporting plates 3-4-6 open or close driven by the external link mechanism 3-5 and the four-link mechanisms 3-4-2.

In the foregoing structures, small filtration pores are distributed on the filtering cartridge 3-4-1 and the supporting plates 3-4-6. The filtration pores may be used to filter a liquid, to prevent medical waste from being soaked in a condensate, and facilitate even steam penetration and heat conduction in a sterilization treatment process.

In addition, a blow-off apparatus 3-6 is further provided on the discharging gate 3-1, and the blow-off apparatus 3-6 is connected to a blow-off pipe by using a flexible hose.

Further, a heat preservation and insulation layer is provided outside the sterilization and discharging chamber 3.

The apparatus uses an electrical control system to control the working of the three chambers, and an operation panel is installed in an independent control cabinet.

A use procedure of the apparatus integrating medical waste crushing and steam treatment is as follows.

(1) Feeding. Materials are automatically fed, and are poured from the feeding gate 1-1 at the top of the apparatus.

(2) Pre-vacuumization. Pre-vacuumization is started after the feeding gate 1-1 is closed, and the pre-vacuumization is performed for three to five minutes.

(3) Crushing. Crushing is started after the feeding gate 1-1 is closed and the pre-vacuumization ends. The shredder works at a preset time interval and in a preset operation direction, ensuring that all waste can enter the shredder.

(4) Steam sterilization treatment. Steam is input to the sterilization chamber, and the temperature in the sterilization chamber is increased to a preset temperature. Temperature monitoring is performed in a lower portion of the sterilization and discharging chamber 3, and the temperatures and the pressures in both the upper and lower working areas in the sterilization chamber are under control and in balance. The medical waste stays in the sterilization chamber for a preset time under the preset temperature and a preset pressure, completing a steam sterilization treatment process.

(5) Cooling. Cold water is injected into the sterilization chamber, and the temperature in the sterilization chamber decreases to approximately 80° C. Then an exhaust valve is opened, and the pressure in the sterilization chamber decreases to the normal pressure.

(6) Drainage. Cooling water and condensate water are discharged.

(7) Post-vacuumization. Before the gate is opened, sterilized waste and remaining steam are condensed by vacuumization, and crushed waste is fully dried.

(8) Discharging. First air is returned so that the pressure in the sterilization chamber reaches the normal pressure, and the lower chamber gate is opened, automatically pouring out the waste.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A quick blade repair and replacement enabled apparatus integrating medical waste crushing and steam treatment, the apparatus being an integrally assembled vertical structure capable of being disassembled, wherein the apparatus sequentially comprises three chamber bodies, connected into a whole by using flanges and bolts, of a feeding and stirring chamber (1), a shredding chamber (2), and a sterilization and discharging chamber (3) from top to bottom, the three chamber bodies internally form a communicating sealable space, and are vertically placed on a support frame (4) as a whole, and a power mechanism is provided outside a chamber body of the shredding chamber; a top end and a bottom end of the shredding chamber (2) are respectively opening flange structures, a left side and a right side of the chamber body (2-1) of the shredding chamber are respectively provided with repair gates (2-3), and a rotary blade assembly and a stationary blade assembly are provided in the shredding chamber; two ends of a rotary blade shaft (2-2) of the rotary blade assembly are respectively fixed on the repair gates by using bearings, bearing supports are connected to the repair gates (2-3) as a whole, one end of the rotary blade shaft extends out of the chamber body of the shredding chamber, and is connected to the power mechanism (2-5), and the power mechanism uses a sprocket or a gear transmission structure; rotary blades (2-6) of the rotary blade assembly are mounted on the rotary blade shaft, blade claws of adjacent rotary blades are arranged by staggering at an angle, and rotary blades on the different rotary blade shafts are alternately arranged; stationary blades (2-7) of the stationary blade assembly are fixed on an inner wall of the chamber body (2-1) of the shredding chamber by using pressing plates (2-8), and the pressing plates are secured from outside of the chamber body of the shredding chamber by using bolts; and the rotary blades (2-6) and the stationary blades (2-7) are alternately arranged.

2. The quick blade repair and replacement enabled apparatus integrating medical waste crushing and steam treatment according to claim 1, wherein the repair gates of the shredding chamber are quick dismounting and mounting structures, gate plates of the repair gates (2-3) are connected and fixed to the chamber body of the shredding chamber by using bolts, and the gate plates are provided with the bearing supports (2-9) for mounting the bearings of the rotary blade shaft and cover plates for securing and sealing the bearings, wherein the cover plate at one end of the rotary blade shaft is an open cover (2-10), and the rotary blade shaft passes through the open cover and is connected to the power mechanism outside the chamber body of the shredding chamber, and the cover plate at the other end is a closed cover (2-11), for sealing the end of the rotary blade shaft.

3. The quick blade repair and replacement enabled apparatus integrating medical waste crushing and steam treatment according to claim 2, wherein two rotary blade assemblies and two stationary blade assemblies form a double-shaft and double-roller structure in the shredding chamber; the two rotary blade assemblies comprise the rotary blade shafts (2-2) and the rotary blades (2-6) and rotary blade separation rings mounted on the rotary blade shafts, and the rotary blades and the rotary blade separation rings are alternately mounted along axial direction of the rotary blade shaft; the two stationary blade assemblies comprise the stationary blades (2-7) and stationary blade separation rings, and the stationary blades and the stationary blade separation rings are alternately mounted parallel to axial direction of the rotary blade shaft; the rotary blades (2-6) are designed to be disk-shaped, and plural blade claws are provided on a circumference of the rotary blades, and the stationary blades (2-7) are designed to be sector-shaped; and the two stationary blade assemblies are respectively alternately combined with the rotary blades and the rotary blade separation rings of the two rotary blade assemblies.

4. The quick blade repair and replacement enabled apparatus integrating medical waste crushing and steam treatment according to claim 3, wherein the rotary blades and the rotary blade separation rings are designed as a whole or designed as two parts entirely separate and independent, and the stationary blades and the stationary blade separation rings are designed as a whole or designed as two parts entirely separate and independent.

5. The quick blade repair and replacement enabled apparatus integrating medical waste crushing and steam treatment according to claim 4, wherein a chamber bottom of the feeding and stirring chamber is designed as an opening flange, a chamber top of the feeding and stirring chamber is provided with a quick-opening feeding gate (1-1), a feeding gate opening and closing mechanism and a secure interlocking mechanism (1-3) ensuring secure opening and closing of the feeding gate are provided outside a chamber body (1-2) of the feeding and stirring chamber, and a pressing and stirring mechanism (1-4) is provided inside the chamber body of the feeding and stirring chamber, wherein a stirring shaft of the pressing and stirring mechanism is obliquely mounted on a wall of the chamber body of the feeding and stirring chamber by using a bearing, an internal end of the stirring shaft is inside the chamber body of the feeding and stirring chamber, an external end of the stirring shaft is outside the chamber body of the feeding and stirring chamber, the external end of the stirring shaft is connected to a motor by using a reducer, and the internal end of the stirring shaft is fixed to a stirring paddle.

6. The quick blade repair and replacement enabled apparatus integrating medical waste crushing and steam treatment according to claim 4, wherein a top end of the sterilization and discharging chamber is designed as an opening flange, a bottom of the sterilization and discharging chamber is provided with a quick-opening discharging gate (3-1), a discharging gate opening and closing mechanism (3-3) and a secure interlocking mechanism ensuring secure opening and closing of the discharging gate are provided outside a chamber body (3-2) of the sterilization and discharging chamber, a tray filtering gating mechanism (3-4) is provided inside the chamber body of the sterilization and discharging chamber, and a blow-off apparatus (3-6) is provided on the quick-opening discharging gate.

7. The quick blade repair and replacement enabled apparatus integrating medical waste crushing and steam treatment according to claim 3, wherein a chamber bottom of the feeding and stirring chamber is designed as an opening flange, a chamber top of the feeding and stirring chamber is provided with a quick-opening feeding gate (1-1), a feeding gate opening and closing mechanism and a secure interlocking mechanism (1-3) ensuring secure opening and closing of the feeding gate are provided outside a chamber body (1-2) of the feeding and stirring chamber, and a pressing and stirring mechanism (1-4) is provided inside the chamber body of the feeding and stirring chamber, wherein a stirring shaft of the pressing and stirring mechanism is obliquely mounted on a wall of the chamber body of the feeding and stirring chamber by using a bearing, an internal end of the stirring shaft is inside the chamber body of the feeding and stirring chamber, an external end of the stirring shaft is outside the chamber body of the feeding and stirring chamber, the external end of the stirring shaft is connected to a motor by using a reducer, and the internal end of the stirring shaft is fixed to a stirring paddle.

8. The quick blade repair and replacement enabled apparatus integrating medical waste crushing and steam treatment according to claim 3, wherein a top end of the sterilization and discharging chamber is designed as an opening flange, a bottom of the sterilization and discharging chamber is provided with a quick-opening discharging gate (3-1), a discharging gate opening and closing mechanism (3-3) and a secure interlocking mechanism ensuring secure opening and closing of the discharging gate are provided outside a chamber body (3-2) of the sterilization and discharging chamber, a tray filtering gating mechanism (3-4) is provided inside the chamber body of the sterilization and discharging chamber, and a blow-off apparatus (3-6) is provided on the quick-opening discharging gate.

9. The quick blade repair and replacement enabled apparatus integrating medical waste crushing and steam treatment according to claim 2, wherein a chamber bottom of the feeding and stirring chamber is designed as an opening flange, a chamber top of the feeding and stirring chamber is provided with a quick-opening feeding gate (1-1), a feeding gate opening and closing mechanism and a secure interlocking mechanism (1-3) ensuring secure opening and closing of the feeding gate are provided outside a chamber body (1-2) of the feeding and stirring chamber, and a pressing and stirring mechanism (1-4) is provided inside the chamber body of the feeding and stirring chamber, wherein a stirring shaft of the pressing and stirring mechanism is obliquely mounted on a wall of the chamber body of the feeding and stirring chamber by using a bearing, an internal end of the stirring shaft is inside the chamber body of the feeding and stirring chamber, an external end of the stirring shaft is outside the chamber body of the feeding and stirring chamber, the external end of the stirring shaft is connected to a motor by using a reducer, and the internal end of the stirring shaft is fixed to a stirring paddle.

10. The quick blade repair and replacement enabled apparatus integrating medical waste crushing and steam treatment according to claim 2, wherein a top end of the sterilization and discharging chamber is designed as an opening flange, a bottom of the sterilization and discharging chamber is provided with a quick-opening discharging gate (3-1), a discharging gate opening and closing mechanism (3-3) and a secure interlocking mechanism ensuring secure opening and closing of the discharging gate are provided outside a chamber body (3-2) of the sterilization and discharging chamber, a tray filtering gating mechanism (3-4) is provided inside the chamber body of the sterilization and discharging chamber, and a blow-off apparatus (3-6) is provided on the quick-opening discharging gate.

11. The quick blade repair and replacement enabled apparatus integrating medical waste crushing and steam treatment according to claim 1, wherein a chamber bottom of the feeding and stirring chamber is designed as an opening flange, a chamber top of the feeding and stirring chamber is provided with a quick-opening feeding gate (1-1), a feeding gate opening and closing mechanism and a secure interlocking mechanism (1-3) ensuring secure opening and closing of the feeding gate are provided outside a chamber body (1-2) of the feeding and stirring chamber, and a pressing and stirring mechanism (1-4) is provided inside the chamber body of the feeding and stirring chamber, wherein a stirring shaft of the pressing and stirring mechanism is obliquely mounted on a wall of the chamber body of the feeding and stirring chamber by using a bearing, an internal end of the stirring shaft is inside the chamber body of the feeding and stirring chamber, an external end of the stirring shaft is outside the chamber body of the feeding and stirring chamber, the external end of the stirring shaft is connected to a motor by using a reducer, and the internal end of the stirring shaft is fixed to a stirring paddle.

12. The quick blade repair and replacement enabled apparatus integrating medical waste crushing and steam treatment according to claim 1, wherein a top end of the sterilization and discharging chamber is designed as an opening flange, a bottom of the sterilization and discharging chamber is provided with a quick-opening discharging gate (3-1), a discharging gate opening and closing mechanism (3-3) and a secure interlocking mechanism ensuring secure opening and closing of the discharging gate are provided outside a chamber body (3-2) of the sterilization and discharging chamber, a tray filtering gating mechanism (3-4) is provided inside the chamber body of the sterilization and discharging chamber, and a blow-off apparatus (3-6) is provided on the quick-opening discharging gate.

13. The quick blade repair and replacement enabled apparatus integrating medical waste crushing and steam treatment according to claim 12, wherein the tray filtering gating mechanism (3-4) comprises a filtering cartridge (3-4-1), two four-link mechanisms (3-4-2), four connecting shafts (3-4-5), and two supporting plates (3-4-6); the filtering cartridge (3-4-1) is connected to an inner wall of the chamber body (3-2) of the sterilization and discharging chamber with a gap there between; upper ends of the two four-link mechanisms (3-4-2) are connected to an external link mechanism (3-5) outside the chamber body (3-2) of the sterilization and discharging chamber, the external link mechanism (3-5) is driven by using an air cylinder or an oil cylinder, and lower ends of the two four-link mechanisms are connected to middle edges of the two supporting plates (3-4-6) by using the four connecting shafts (3-4-5); and the supporting plates (3-4-6) are configured to turn at the connecting shafts (3-4-5), the two supporting plates are arranged in bilateral symmetry and placed at a lower end of the filtering cartridge (3-4-1), external ends of the supporting plates (3-4-6) are connected to the inner wall of the chamber body of the sterilization and discharging chamber by using hinges (3-4-4) and are configured to turn at the hinges, and when air or oil in the air cylinder or the oil cylinder expands or is compressed, the supporting plates (3-4-6) open or close driven by the external link mechanism (3-5) and the four-link mechanisms (3-4-2).

14. The quick blade repair and replacement enabled apparatus integrating medical waste crushing and steam treatment according to claim 13, wherein two guide mechanisms (3-4-3) are provided on an outer wall of the filtering cartridge (3-4-1) and the two guide mechanisms (3-4-3) are cooperated with the four-link mechanisms (3-4-2), working ends of the four-link mechanisms (3-4-2) are guided by the two guide mechanisms (3-4-3) to move up and down.

15. The quick blade repair and replacement enabled apparatus integrating medical waste crushing and steam treatment according to claim 13, wherein small filtration pores are distributed on the filtering cartridge (3-4-1) and the supporting plates (3-4-6).

\* \* \* \* \*